US009580327B2

(12) United States Patent
Yilmaz et al.

(10) Patent No.: US 9,580,327 B2
(45) Date of Patent: Feb. 28, 2017

(54) METHOD AND APPARATUS FOR CONSOLIDATION OF GRANULAR SILICON AND MEASURING NON-METALS CONTENT

(71) Applicant: REC Silicon Inc, Moses Lake, WA (US)

(72) Inventors: Sefa Yilmaz, Moses Lake, WA (US); Theodore F. Ciszek, Evergreen, CO (US); Matthew J. Miller, Moses Lake, WA (US); Stein Julsrud, Moses Lake, WA (US)

(73) Assignee: REC Silicon Inc, Moses Lake, WA (US)

( * ) Notice: Subject to any disclaimer, the term of this patent is extended or adjusted under 35 U.S.C. 154(b) by 306 days.

(21) Appl. No.: 14/178,103

(22) Filed: Feb. 11, 2014

(65) Prior Publication Data

US 2015/0225246 A1    Aug. 13, 2015

(51) Int. Cl.
*C01B 33/021*    (2006.01)
*G01N 21/3563*    (2014.01)
(Continued)

(52) U.S. Cl.
CPC ............ *C01B 33/021* (2013.01); *C01B 31/14* (2013.01); *C01B 33/02* (2013.01); *C01B 33/035* (2013.01);
(Continued)

(58) Field of Classification Search
CPC ........ G01N 21/3563; G01N 2021/3595; C01B 33/021; C01B 33/037; C01B 33/02; C01B 33/035; C01B 31/14
(Continued)

(56) References Cited

U.S. PATENT DOCUMENTS

| 4,312,700 A | * | 1/1982 | Helmreich | ............ C04B 35/52 |
| | | | | 117/924 |
| 4,565,600 A | * | 1/1986 | Ricard | .................... C30B 15/08 |
| | | | | 117/23 |

(Continued)

FOREIGN PATENT DOCUMENTS

| GB | 871156 | 6/1961 |
| GB | 871157 | 6/1961 |

(Continued)

OTHER PUBLICATIONS

Boyle, "FT-IR Measurement of Interstitial Oxygen and Substitutional Carbon in Silicon Wafers," *Thermo Fisher Scientific* (2008).
(Continued)

*Primary Examiner* — David Porta
*Assistant Examiner* — Mindy Vu
(74) *Attorney, Agent, or Firm* — Klarquist Sparkman, LLP (57) ABSTRACT

Apparatus and methods for consolidating granular silicon and determining trace elements content of the consolidated silicon are disclosed. Silicon granules are placed in a vessel, and a silicon slug of known purity is embedded at least partially in the granules. The slug is preheated to a temperature sufficient to couple with an induction heater. As the silicon slug melts, silicon granules adjacent the molten silicon also melt. The vessel passes through an induction coil to successively inductively heat and melt regions of the silicon granules from the leading end to the trailing end with each region solidifying as the molten silicon exits the induction coil to provide a multicrystalline silicon ingot. The multicrystalline silicon ingot is sliced into wafers, which are analyzed by low-temperature Fourier transform infrared spectroscopy to determine levels of trace elements in the ingot.

20 Claims, 8 Drawing Sheets (51) Int. Cl.
*C01B 33/037* (2006.01)
*C01B 33/02* (2006.01)
*C01B 33/035* (2006.01)
*C01B 31/14* (2006.01)
*G01N 21/35* (2014.01)

(52) U.S. Cl.
CPC ....... *C01B 33/037* (2013.01); *G01N 21/3563* (2013.01); *G01N 2021/3595* (2013.01)

(58) Field of Classification Search
USPC .................................................. 423/348, 349
See application file for complete search history.

(56) References Cited

U.S. PATENT DOCUMENTS

| | | | |
|---|---|---|---|
| 4,572,848 A * | 2/1986 | Pollak | C04B 35/573 118/271 |
| 5,436,164 A | 7/1995 | Dumler et al. | |
| 5,499,598 A | 3/1996 | Oda | |
| 6,074,476 A | 6/2000 | Hanabe et al. | |
| 6,210,478 B1 | 4/2001 | Bewlay et al. | |
| 2002/0081250 A1 | 6/2002 | Lord | |
| 2008/0299291 A1 | 12/2008 | Weidhaus et al. | |
| 2014/0083638 A1 * | 3/2014 | Waniuk | H05B 6/26 164/47 |

FOREIGN PATENT DOCUMENTS

| | | |
|---|---|---|
| GB | 2207061 A | 1/1989 |
| GB | 2207062 B | 1/1989 |

OTHER PUBLICATIONS

Muhlbauer, A. "Innovative Induction Melting Technologies: A Historical Review," *International Scientific Colloquium, Modelling for Material Processing*, Riga, pp. 13-20 (Jun. 8-9, 2006).

Porrini, M., "Measurement of Boron and Phosphorus Concentration in Silicon by Low-Temperature FTIR Spectroscopy," *Springer Link*, vol. 81, Issue 6, pp. 1187-1190, Abstract only (Nov. 2005).

REC Silicon Inc., "White Paper: Granular Consolidation and Calculation Method for Acceptors/Donors and Carbon," 1 page (2013).

* cited by examiner

METHOD AND APPARATUS FOR CONSOLIDATION OF GRANULAR SILICON AND MEASURING NON-METALS CONTENT

FIELD

This disclosure concerns an apparatus and methods for consolidating granular silicon and determining non-metals content of the consolidated silicon.

BACKGROUND

Granular silicon is used, for example, for making silicon ingots, which subsequently are sliced into silicon wafers. The granular silicon is required to have a very high purity. However, granular silicon presents technical challenges in the characterization of its material properties. These challenges increase the characterization cost, which in turn increases the production cost. For example, determining product variability is particularly challenging when dealing with very high purity materials, such as electronic-grade silicon. Present methods of characterizing granular material may not produce meaningful results and/or may be prohibitively expensive. Thus, there is a need for a reliable, relatively rapid, cost-effective method for characterizing granular silicon.

SUMMARY

This disclosure concerns an apparatus and methods for consolidating granular silicon and determining levels of trace elements in the consolidated silicon. The granular silicon is a representative sample of a larger batch of granular silicon. Embodiments of a method for consolidating granular silicon include placing a volume of silicon granules in a vessel, such as a metal boat, having an upwardly opening cavity with a leading end and a trailing end. The silicon granules may have an average diameter of less than 10 mm. The volume of silicon granules may have a mass of 10-40 g. A silicon slug of known purity is embedded at least partially in the volume of silicon granules near the leading end, and the vessel is positioned to pass through an induction coil of an induction heater.

The vessel may be placed within a shield device. In one embodiment, the shield device is configured to extend horizontally through the induction coil. In another embodiment, the shield device encloses the vessel and the induction coil.

The silicon slug is heated with a preheater, such as a conductive silicon carbide preheater, to a temperature sufficient to couple the silicon slug with the induction heater, and then inductively heated to a temperature sufficient to melt at least a portion of the slug and form a silicon melt. In some embodiments, the silicon slug has a diameter of at least 8 mm and/or a mass of 0.6-5 g. Advantageously, the silicon slug has a smallest dimension that is larger than an average diameter of the silicon granules. The slug may be preheated to a temperature of at least 1000° C., thereby enabling the slug to couple to the induction coil.

Once the silicon slug has at least partially melted, the vessel or the induction coil is moved generally horizontally such that the vessel passes through the induction coil to successively inductively heat and melt regions of the volume of silicon granules from the leading end to the trailing end of the vessel, with each region solidifying as the molten silicon exits the induction coil to provide a multicrystalline silicon ingot.

Embodiments of a method for determining trace element concentrations in the multicrystalline silicon ingot include removing the multicrystalline silicon ingot from the vessel, slicing a wafer from the ingot, and determining levels of trace elements in the wafer, e.g., by low-temperature Fourier transform infrared spectroscopy. In some embodiments, the trace elements include one or more of boron, phosphorus, carbon, aluminum, and oxygen. The determined trace element level may be mathematically corrected to compensate for trace elements within the silicon slug and determine a corrected level of the trace element in the silicon granules.

Embodiments of a granule consolidation apparatus include a vessel having a surface that defines an upwardly opening cavity, an induction heater comprising an induction coil defining an axially extending passageway sized such that the vessel can pass through the passageway, and a preheater. In some embodiments, one of the vessel and the induction coil is configured to move axially relative to the other component. The preheater may be configured to move axially relative to the induction coil.

The upwardly opening cavity of the vessel may have a capacity of ≤500 cm$^3$. In some embodiments, the upwardly opening cavity has a length of at least 10 cm, such as from 10 cm to 25 cm, and/or a greatest width from 5 mm to 15 mm. In some embodiments, the vessel further comprises an inlet, an outlet, and an internal fluid passageway discrete from the cavity and in communication with the inlet and the outlet. Advantageously, the vessel is constructed of copper, silver, or gold.

The preheater may have a ring configuration defining an axially extending passageway sized such that the vessel can pass through the passageway. In some embodiments, the preheater is a silicon carbide preheater. Advantageously, an insulation layer may be provided around an outer surface of the preheater.

In some embodiments, the granule consolidation apparatus further includes a shield device configured to surround the vessel or to surround the vessel and the induction coil. Advantageously, the passageway defined by the induction coil is sized such that the vessel, and optionally the shield device, can pass through the passageway. If the preheater has a ring configuration, the passageway defined by the preheater also is sized such that the vessel, and optionally the shield device, can pass through the passageway.

The foregoing and other features and advantages of the invention will become more apparent from the following detailed description, which proceeds with reference to the accompanying figures.

DETAILED DESCRIPTION

This disclosure concerns embodiments of a method and apparatus for consolidating silicon granules in a form suitable for determining purity of the silicon. Polysilicon granules are melted and consolidated into a multicrystalline ingot using a boat zoning process. The resulting multicrystalline ingot can be sliced into wafers and analyzed, e.g., by low-temperature Fourier transform infrared spectroscopy, to determine levels of trace elements in the granular silicon.

I. TERMS AND ABBREVIATIONS

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

In order to facilitate review of the various embodiments of the disclosure, the following explanations of specific terms and abbreviations are provided:

Boat zoning: Similar to a float zoning process except silicon is contained in contact with a vessel as zones of the silicon are melted along the length of the vessel.

Boat zoner: A boat zoning apparatus.

FZ: float zone

Induction heating: Heating an electrically conductive object (typically a metal or metalloid object) by electromagnetic induction. An induction heater includes an electromagnet through which an alternating current is passed. The magnetic field induces eddy currents within the object, and resistance within the metal/metalloid leads to heating of the material.

Inductive coupling: Two conductors are inductively coupled when a current flowing through one conductor induces a voltage across the other conductor through electromagnetic induction.

Ingot: As used herein, the term "ingot" refers to an essentially solid mass of material (i.e., silicon) formed by melting granular silicon and then solidifying the molten silicon. The ingot has a form or geometry suitable for subsequent analysis. In one embodiment, the ingot is in the form of a rod, e.g., having a substantially circular or elliptical cross-section. In another embodiment, the ingot may be a film having a substantially rectangular cross-section. It is to be understood that the ingot may have an irregular surface.

LTFTIR: low-temperature Fourier transform infrared (spectroscopy)

ppba: parts per billion atomic, i.e., atoms per billion atoms ppma: parts per million atomic, i.e., atoms per million atoms ppta: parts per trillion atomic, i.e., atoms per trillion atoms RF: radiofrequency Slug: A lump, disc, sphere, cube, or cylinder of essentially solid material

II. CONSOLIDATION OF GRANULAR SILICON

Consolidation of granular silicon into a solid ingot form facilitates subsequent characterization of the silicon. The granular silicon may be a representative sample of granular silicon from a larger batch of silicon. Embodiments of a method for consolidating granular silicon into a ingot comprise inductively melting the silicon granules and subsequently allowing the silicon melt to solidify into a multicrystalline silicon ingot.

Induction melting conditions are a function of physical, electrical and magnetic properties of the material being melted. Thickness/size of the material, electrical resistivity, relative magnetic permeability, and the frequency used affect the melting process.

Figure 1:
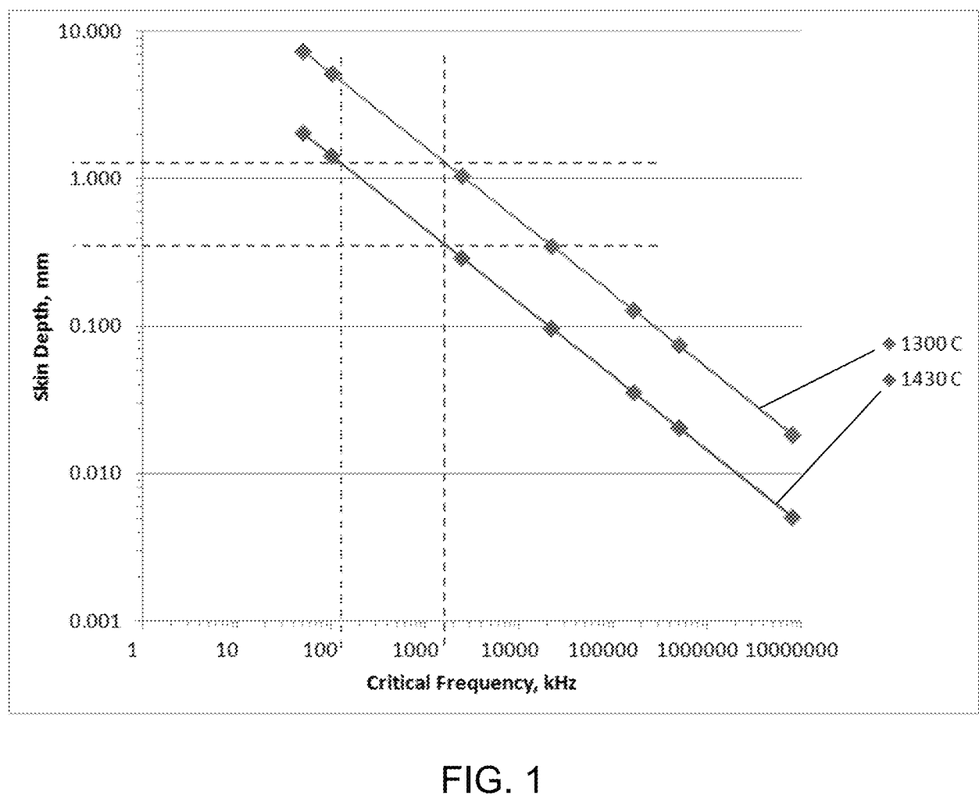
FIG. 1 is a graph of skin depth versus critical frequency, which shows the effect of preheating temperature on the critical frequency for melting silicon granules of a given size.

The relationship between critical frequency and skin depth is shown graphically in FIG. 1 for 1300° C. and 1430° C. A decreased skin depth means that eddy currents induced in an object are concentrated nearer the object's surface, which facilitates inductive heating of the object's surface. With respect to silicon, skin depth decreases as frequency increases and/or as the object's temperature increases.

A theoretical evaluation illustrates the relationship between silicon granule size, preheating temperature, and the critical frequency required for inductive coupling. The results are shown in Table 1. (The resistivity values for silicon used in the calculation of the critical frequency were obtained from Magomedov et al., "Thermal and Electrical Conductivities of Silicon in Solid and Liquid States," Institute of Physics Daghestan Scientific Center of RAS, Makhachkala 367003, Russia, circa 2006.)

TABLE 1

| Size, mm | Preheating Temp., ° C. | Critical Frequency, kHz |
|---|---|---|
| 2 | 800 | 27,000 |
| 2 | 1300 | 15,100 |
| 2 | 1415 | 840 |
| 12 | 800 | 750 |

TABLE 1-continued

| Size, mm | Preheating Temp., ° C. | Critical Frequency, kHz |
|---|---|---|
| 12 | 1300 | 400 |
| 12 | 1415 | 20 |

As shown in Table 1, when silicon granules with a 2-mm diameter (8-10 U.S. mesh size) are preheated to 800° C., the critical frequency for direct inductive coupling is 27 MHz. When preheated to 1415° C. (the melting point of silicon), the coupling frequency is reduced to 840 kHz. Typical practical induction frequencies are less than 5 MHz. Thus, small granules must be heated to high temperatures to couple at a practical frequency. Increasing the granule size reduces the coupling frequency. For example, granules with a 12-mm diameter heated to 1300° C. have a coupling frequency of 400 kHz. However, smaller granules (e.g., 2-5 mm) may be desirable for subsequent uses.

Because coupling frequency is size and temperature dependent, including a slug having a smallest dimension that is larger than an average diameter of the silicon granules allows inductive coupling to occur at a lower temperature and frequency. As the slug melts, silicon granules adjacent the melt are heated by the molten silicon to a temperature sufficient for inductive coupling and also melt. Because the molten slug becomes a part of the resulting consolidated silicon ingot, a silicon slug of known purity is used. In particular, the levels of boron, phosphorus, and carbon are determined before the slug is used. The silicon slug desirably comprises less than 10 ppta boron and phosphorus, and less than 10 ppba carbon. Additional impurity levels, e.g., aluminum and/or oxygen, also may be known.

Figure 2:
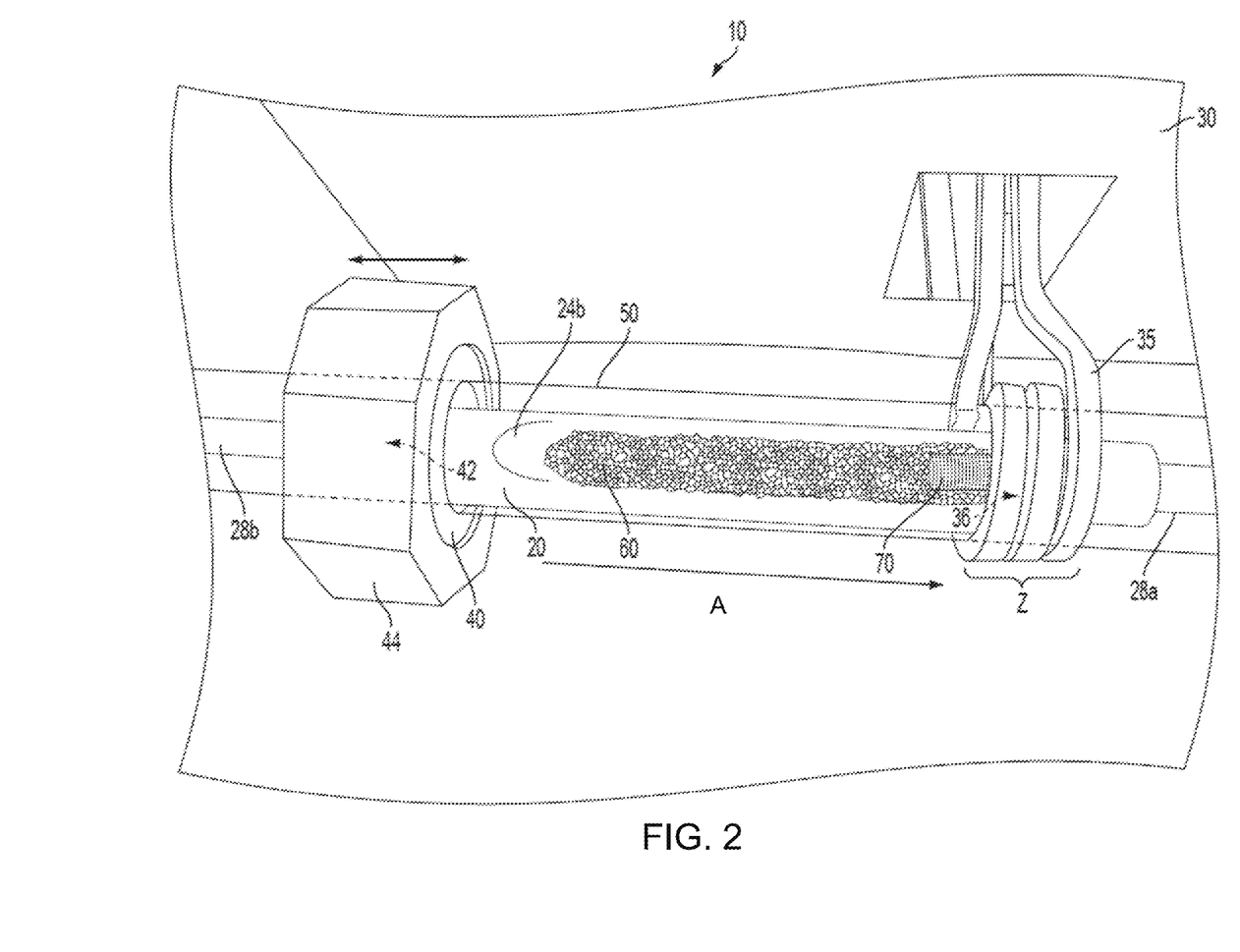
FIG. 2 is a perspective view of one embodiment of an apparatus for consolidating silicon granules by induction melting.

A sample of silicon granules is prepared for characterization (e.g., trace element determination) by forming a silicon ingot via induction melting and consolidation of the granules. One embodiment of a granule consolidation apparatus 10 is shown in FIG. 2. The exemplary granule consolidation apparatus 10 includes a vessel 20, an induction heater 30 comprising an induction coil 35, a preheater 40, and a shield device 50 for providing a controlled environment surrounding vessel 20. A volume of silicon granules 60 is placed within the vessel 20, and a silicon slug 70 is partially embedded within the silicon granules 60.

Figure 3:
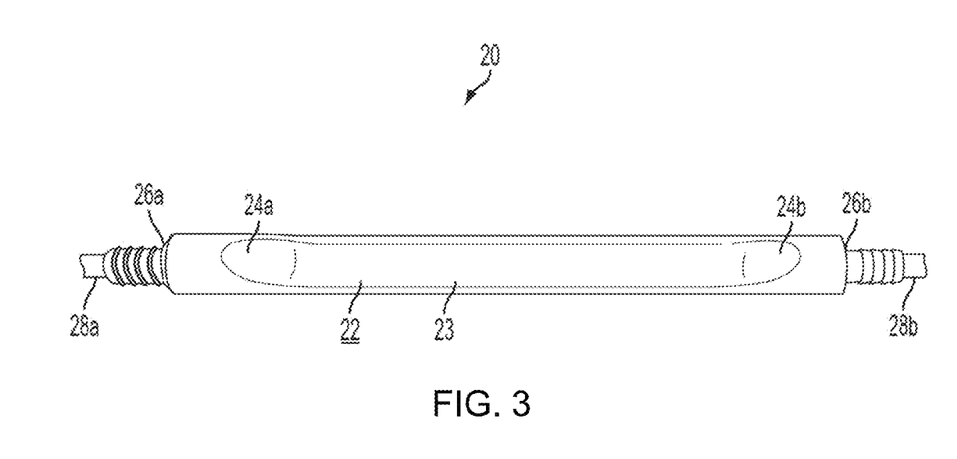
FIG. 3 is a perspective view of one embodiment of a vessel for use with the apparatus of FIG. 2.
Figure 4:
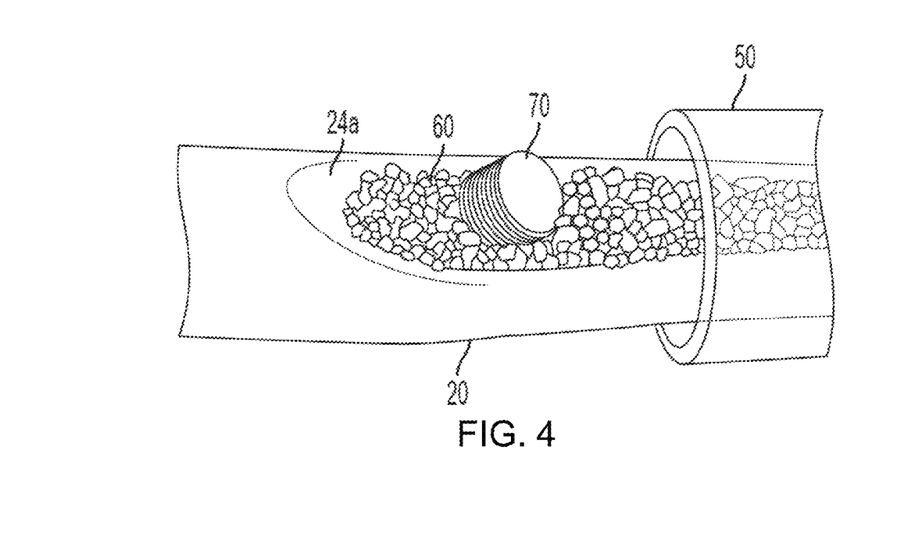
FIG. 4 is an enlarged partial perspective view of the vessel of FIG. 3 and the shield device of FIG. 2, with the vessel containing a volume of silicon granules and a slug.

With reference to FIGS. 2-4, vessel 20 has a surface 22 that defines an upwardly opening cavity 23 to receive silicon granules 60 and slug 70. The cavity 23 defined by surface 22 has a leading end 24a and a trailing end 24b. Vessel 20 may be cooled during the silicon melting and consolidation process. In some embodiments, vessel 20 defines an internal chamber or fluid passageway (not shown) having an inlet 26a and an outlet 26b. Conduits 28a, 28b define axially extending passageways (not shown) that communicate with inlet 26a and outlet 26b, respectively, such that a cooling fluid can flow through conduit 28a into vessel 20 via inlet 26a, and exit vessel 20 through outlet 26b and conduit 28b. Suitable cooling fluids include water or ethylene glycol/water mixtures. Cooling the vessel 20 reduces contamination of the silicon melt by the vessel material and/or prevents the silicon ingot from sticking to the vessel surface 22.

In some embodiments, vessel 20 is thermally conductive. Vessel 20 may be constructed of a metal. Suitable metals include copper, silver, and gold. Advantageously, the vessel is constructed of copper. The vessel may be a unitary piece.

The upwardly opening cavity 23 is dimensioned to receive a quantity of silicon granules sufficient to form an ingot that subsequently can be characterized, e.g., to determine its purity. In some embodiments, the upwardly opening cavity defined by surface 22 has a capacity of ≤500 cm$^3$. The upwardly opening cavity 23 may have a length of at least 10 cm, such as a length of 10-25 cm or 15-20 cm, thereby enabling formation of an ingot having a length of 10-20 cm. In some non-limiting arrangements, the upwardly opening cavity 23 has a greatest width from 5 mm to 15 mm, such as a width from 8-10 mm.

During operation a volume of silicon granules 60 is placed in the upwardly opening cavity 23. In some embodiments, the volume of silicon granules has a mass from 10 g to 40 g, such as a mass of 20-40 g or 30-40 g. A silicon slug 70 of known purity is placed near the leading end 24a of the upwardly opening cavity 23. Advantageously, the silicon slug 70 is partially embedded in the volume of silicon granules 60. The silicon slug advantageously has a smaller mass than the volume of silicon granules. For example, when using 10-40 g of silicon granules, the slug may have a mass of 0.6-5 g, such as mass of 1-3 g, or 1.5-2.5 g. Advantageously, the silicon slug 70 has a minimum dimension that is larger than an average diameter of the silicon granules. The silicon slug 70, having a mass of 0.6-5 g, may have a generally spherical or cylindrical shape with a diameter of at least 8 mm, such as a diameter of 8-20 mm, 8-15 mm, 8-12 mm, or 10-12 mm.

The granule consolidation apparatus 10 includes an induction heater 30 comprising an induction coil 35. The induction heater 30 is configured to provide an alternating current to the induction coil 35, thereby generating an electromagnetic field. The induction heater 30 may include any suitable power source (not shown) including, but not limited to, a radio frequency (RF) generator. In some embodiments, the induction heater 30 is operated at 300-3000 kHz, such as 300-1700 kHz, 300-1500 kHz, 600-1700 kHz, or 700-1500 kHz. In one example, a 15 kW RF generator was operated at a frequency of 1.2 MHz.

The illustrated induction coil 35 is generally in the shape of a cylinder and defines an axially extending passageway 36. The coil 35 has an inner diameter sized such that the vessel 20 can pass through the induction coil. If a shield device 50 is utilized, then the induction coil 35 has a sufficiently large inner diameter to accommodate the shield device. In another embodiment (not shown), a shield device is configured to accommodate the vessel and the induction coil.

In some embodiments, the induction coil 35 is configured to provide a melting zone Z having a length of 20-30 mm. The induction coil may include 2-20 turns, such as 3-20 turns, 3-10 turns, or 3-5 turns. The number of turns may be selected, in part, based on the desired power, the desired frequency, the efficiency of power transfer, and/or the desired melt zone length. In some arrangements, the induction coil is constructed with tubing or wire having a substantially square cross-section as shown in FIG. 2. The square cross-section facilitates close packing of the coils and a consistent distance from the vessel. In other embodiments, the tubing or wire forming the induction coil may have a different cross-section, such as a substantially circular or elliptical cross-section. The induction coil 35 may be constructed of any material capable of producing an electromagnetic field when an alternating current is passed through the induction coil. Suitable materials include, but are not limited to, copper, silver, and gold. The granule consolidation apparatus 10 is configured so that one of the vessel 20 and the induction coil 35 can move relative to the other component. In some arrangements, the induction coil 35 is in a fixed position, and the vessel 20 is movable axially (e.g., along a generally horizontal axis as indicated by arrow A).

The granule consolidation apparatus 10 includes a preheater 40. The illustrated preheater 40 has a hollow cylindrical or ring configuration with an inner diameter defining an axially extending passageway 42 sized such that the vessel 20 can pass through the preheater. If a shield device 50 as shown in FIG. 2 is utilized, then the preheater 40 has a sufficiently large inside diameter to accommodate the shield device. The shield device 50 prevents contamination of the granules and/or resulting silicon ingot by the preheater 40 and the ambient air. In another embodiment (not shown), the shield device may be a process chamber configured to accommodate the vessel, the induction coil, and the preheater.

The granule consolidation apparatus 10 is configured so that at least one of the induction coil 35 and the preheater 40 can move relative to the other component, typically in a generally horizontal manner. Additionally, the apparatus 10 is configured so that at least one of the preheater 40 and the vessel 20 can move relative to the other component, typically in a generally horizontal manner. As the heating process begins, the preheater 40 may be positioned proximate to and upstream of the induction coil 35. As the preheater 40 couples with the induction coil 35, it is heated inductively. In some embodiments, the preheater 40 comprises silicon carbide, such as a conductive silicon carbide. The silicon carbide may be silicon doped to provide a higher electrical conductivity for induction heating. The preheater 40 radiatively heats the silicon slug 70 to a temperature sufficient for the slug to directly couple to the RF induction coil 35. After the slug is coupled to the RF induction coil 35, the preheater is moved away from the coil.

In some arrangements, an insulation layer 44 is provided around the outer surface of the preheater 40. The insulation layer 44 reduces heat loss to the surrounding environment and/or helps to inwardly focus heat produced by the preheater 40. Suitable insulating materials include, but are not limited to, rigid or blanket-like structures composed of mixtures of low density alumina and silica.

The granule consolidation apparatus 10 may comprise a shield device 50, e.g., as shown in FIG. 2. In some embodiments, the shield device 50 has a hollow cylindrical or tube configuration with an inner diameter greater than an outer diameter of the vessel 20, and an outer diameter smaller than the diameter of passageway 36 defined by the induction coil 35. The shield device 50 also may have an outer diameter smaller than the diameter of passageway 42 defined by the preheater 40. Advantageously, the shield device 50 has a length greater than a length of the vessel 20. The shield device 50 provides a controlled environment within its confines. A "controlled environment" means that the environment within the shield device 50 is substantially protected from outside contamination. The shield device 50 may be purged with an inert gas (e.g., argon) throughout the heating process, to minimize contamination from elements in air such as oxygen and carbon. The shield device may be sealed by any suitable means (e.g., O-ring seals to machined metal end fixtures) before the heating process begins. The shield device 50 may provide additional thermal control by retaining heat, shielding the contents within its confines from drafts, and/or minimizing undesirable temperature variations. The shield device 50 is constructed of a material that will tolerate the operating temperatures without melting and without imparting contamination to the silicon ingot. In the illustrated embodiment, the shield device 50 is a transparent quartz tube. Other suitable materials may include alumina or silicon carbide. Alternatively, the vessel and induction coil can be located within a larger shield device, such as a process chamber, e.g., a metal chamber with viewing ports.

The granule consolidation apparatus 10 is operable to melt silicon granules 60 and form a multicrystalline silicon ingot. A volume of silicon granules 60 is placed into the upwardly opening cavity 23 defined by surface 22 of the vessel 20. In some embodiments, the silicon granules 60 have an average diameter of ≤10 mm, such as a diameter of 0.1-10 mm, 0.1-5 mm, 0.5-4 mm, 1-3 mm, 1-2 mm, 10 mm, 5 mm, 3 mm, or 2 mm. A silicon slug 70 of known purity is at least partially embedded within the volume of silicon granules 60 near a leading end 24a of the upwardly opening cavity 23.

Optionally, the vessel 20 is placed within a shield device, such as the shield device 50 shown in FIG. 2. The vessel 20 is positioned such that it can pass through the induction coil 35 of the induction heater 30. Typically, the vessel 20 is positioned to pass generally horizontally through the passageway 36 of induction coil 35. If a shield device is used, the shield device may be positioned such that it extends through the induction coil 35. After insertion of the vessel, the interior of the shield device may be purged with an inert gas and then sealed.

A cooling fluid may be utilized to cool the vessel 20. In the illustrated apparatus, the cooling fluid passes through conduit 28a and through inlet 26a, which is in fluid communication with the internal chamber of the vessel 20. The cooling fluid flows through the chamber and exits the vessel 20 through outlet 26b and conduit 28b. In some examples, the cooling fluid is water.

The vessel 20 is positioned so that the leading end 24a is proximate to and upstream of the induction coil 35. To initiate the consolidation process, the preheater 40 is positioned proximate to and upstream of the induction coil 35 so that the preheater 40 can couple with the induction coil 35 and impart heat to the silicon slug 70. Power is supplied to the induction heater 30 at a frequency of 300-3000 kHz. The temperature of the preheater 40 is increased to a temperature sufficient to inductively couple the preheater to the induction heater 30. In some examples, a silicon carbide preheater was heated until it was red hot (i.e., ~1,000° C.) and maintained at that temperature for 5 minutes. The inductively coupled preheater 40 heats the silicon slug 70 to a temperature sufficient to inductively couple the slug to the induction heater 30. In some embodiments, the silicon slug 70 is preheated by to a temperature of at least 1000° C., such as a temperature from 1000° C. to 1400° C., or a temperature from 1300° C. to 1400° C. When the slug 70 has inductively coupled to the induction heater 30, the preheater 40 may be moved away from the induction coil 35, for example to the position shown in FIG. 2. The vessel 20 is moved relative to the induction coil 35 so that the silicon slug 70 is positioned within the induction coil 35. The inductively coupled silicon slug 70 continues to heat and at least a portion of the slug melts, thereby forming a silicon melt. The silicon melt also inductively couples to the induction heater 30. Silicon granules 60 adjacent the molten silicon melt and inductively couple to the induction heater 30.

The vessel 20 or the induction coil 35 is moved generally horizontally such that the vessel 20 passes through the induction coil 35 to successively inductively heat and melt regions, or zones, of the volume of silicon granules 60 from the leading end 24a to the trailing end 24b. In some examples, the induction coil 35 is configured to provide a melting zone Z having a length of 20-30 mm. The vessel 20 is passed through the induction coil 35 at a rate of up to 5 mm/minute, such as a rate of 1-5 mm/minute or 2-4 mm/minute. The rate at which the vessel 20 is passed through the induction coil 35 affects final grain size in the consolidated polysilicon ingot. The grain size varies inversely with the movement rate. Larger grain sizes may be advantageous for subsequent LTFTIR measurements. In some examples, the movement rate was 3 mm/minute.

Figure 5:
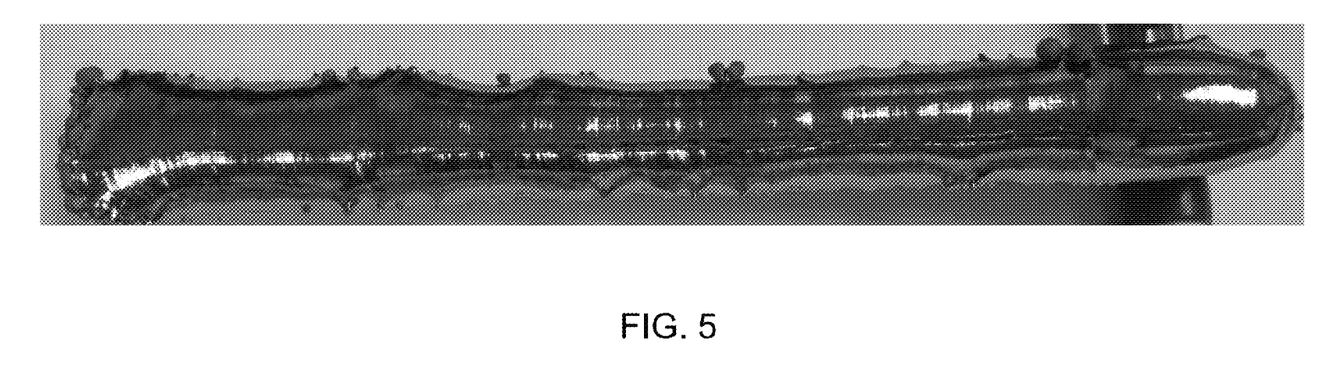
FIGS. 5 and 6 are photographs of exemplary multicrystalline silicon ingots produced by an embodiment of the disclosed consolidation method.
Figure 6:
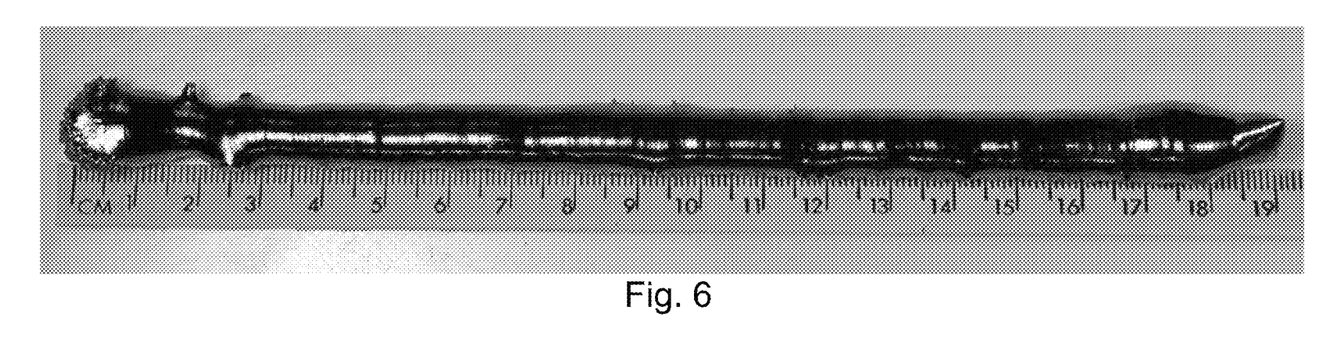

As the vessel 20 passes through the induction coil 35, the trailing edge of the molten zone solidifies as the molten silicon exits the induction coil 35 to provide a multicrystalline silicon ingot in the upwardly opening cavity 23. Concomitantly, new granules are melted into the leading edge of the melt zone. Trace elements, such as impurities and dopants, segregate according to well-known principles. The last zone to freeze follows directional solidification principles as opposed to zone melting mass balance principles (Pfann, *Zone Melting*, $2^{nd}$ edition, 1965, p. 29). FIGS. 5 and 6 are photographs of exemplary multicrystalline silicon ingots produced by an embodiment of the described method. A person of ordinary skill in the art will understand that the geometry of the ingot depends, at least in part, on the geometry of the upwardly opening cavity 23, the size of the upwardly facing cavity 23, and/or the mass of silicon granules used to form the ingot.

A single pass of the vessel through the induction coil provides forward boat zoning. In some embodiments, a reverse zoning, or leveling, pass may be performed immediately after the single pass. The benefit of the leveling pass, based on zone melting theory, is that the initial trace element concentration of the melt ($C_o$) coincides directly with the trace element concentration after the leveling pass if the ingot length is at least 8-9 times the length of the melt zone.

III. TRACE ELEMENT MEASUREMENT

Trace elements, such as non-metals, in granular silicon may be determined by forming a multicrystalline silicon ingot as disclosed herein, and then measuring the trace elements in the multicrystalline silicon ingot, e.g., by using low-temperature Fourier transform infrared spectroscopy (LTFTIR). The ingot is sliced by suitable means and polished into discs or wafers for LTFTIR analysis. In some embodiments, the discs have a thickness of 2-3 mm, such as a thickness of 2.5 mm.

The LTFTIR measured data is plotted as a function of the linear ingot position (x), and the data is fitted by the boat zoning mass balance equation derived from the zone melting principles and accounting for the presence of silicon slug:

$$C_S^I(x) = C_O \left(1 - \left(1 - k \left(\frac{(V_{ZONE} - V_{SLUG}) + \left(C_{SLUG}^I * \frac{V_{SLUG}}{C_O}\right)}{V_{ZONE}}\right)\right) e^{\frac{kx}{l}}\right)$$

where k is the equilibrium segregation coefficient, l is the zone length (mm), x is the linear length of the ingot (mm), $C_s^I(x)$ is the trace element concentration in the solid (g/mm³), I is the trace element, $O_{ZONE}$ is volume of the molten zone (mm³), $V_{SLUG}$ is volume of the solid slug (mm³), $C_{SLUG}^I$ is the trace element concentration in the slug (g/mm³), and $C_o$ is the initial trace element concentration in the melt or granules (g/mm³). Typical k values used for B, P, and C are 0.8, 0.35, and 0.07, respectively (O'Mara et al., "Handbook of Semiconductor Silicon Technology" (1990)).

For certain trace elements (e.g., B, P, C), a minimization function, such as Microsoft Excel® Solver or Goal Seek, can be used to determine a value of $C_o$ that minimizes error between measured and fitted $C_s(x)$ values. The initial concentration of each trace element ($C_o$) represents the concentration of the element in the original sample. The theoretical boat zoning mass balance equation given above takes into account the dilution effect of the slug and the impurity contributions from the slug itself to calculate the initial concentrations of trace elements in the original granular silicon sample.

Both carbon and oxygen have limited solubility in silicon. Carbon precipitates as SiC solid and oxygen precipitates as $SiO_2$ solid in the molten silicon phase when the saturation concentration is reached. LTFTIR does not detect precipitated phases since they are not part of the silicon matrix. Therefore, when fitting the mass balance equation from the starting end to the finished end of the ingot, the data from the starting end typically is more reliable since the liquid has not been sufficiently enriched by carbon or oxygen to reach the saturation limits of either element. Accordingly, starting-end data may be used to determine the concentrations of carbon and oxygen.

Embodiments of the disclosed method for measuring trace elements in granular silicon are sufficiently sensitive to determine trace elements in electronic-grade silicon. For example, some embodiments of the disclosed method provide detection limits in the ppta range for boron and phosphorus, and detection limits in the low ppma range for carbon and oxygen. In some embodiments, boron and phosphorus can be measured at levels as low as 10 ppba, 5 ppba, 1 ppba, or even 0.5 ppba. Carbon can be measured at levels as low as 10 ppma, 5 ppma, 1 ppma, 0.5 ppma, or 0.25 ppma. Other trace elements (e.g., aluminum, antimony, arsenic, gallium, and indium) also may be measured.

IV. EXAMPLES

Example 1

Consolidation of Granular Silicon

Several multicrystalline silicon ingots were produced. For each ingot, a predefined mass of silicon granules (10-40 g) was placed in a water-cooled copper boat (FIG. 3). The granules were evenly distributed throughout the length of the boat. A small, high-purity silicon slug (boron and phosphorus levels in the single ppta range) with dimensions of 10-12 mm diameter and 10 mm long (~1.5-2 g) was partially embedded in the granules at the starting end of the copper boat (see, e.g., FIG. 4). The copper boat was water cooled. A double-helix copper coil with 1.5" (3.8 cm) inner diameter and 25 mm length was used as the induction coil. The copper boat was placed within a quartz shield device having an outer diameter less than 1.5".

The silicon slug was coupled to the inductor by preheating it with a silicon-doped SiC preheater, which also couples with the inductor. The preheater was heated to 1390° C., as measured by a pyrometer, and maintained at that temperature for 10-15 minutes so that the silicon slug reached a temperature sufficient to couple to the induction coil at which time the SiC preheater was moved away from the induction coil. Once the slug began to melt, the melt was readily coupled with the inductor, which subsequently melted silicon granules within the melt zone (approximately 20 mm long as approximated from the length of the induction coil). Within the melt zone, the liquid was well mixed.

The boat and quartz shield were moved through the induction coil using a linear transfer mechanism attached to the boat at a slow speed, ~3 mm/minute. As the melt traveled out of the coil, the liquid rapidly froze on the cold boat, and trace elements segregated according to well-known segregation principles. At the same time, new granules were melted into the liquid zone at they entered into the induction coil.

The ingots were readily removed from the copper boat without sticking. Exemplary ingots are shown in FIGS. 5 and 6.

Example 2

Trace Elements Analysis—I

Figure 7:
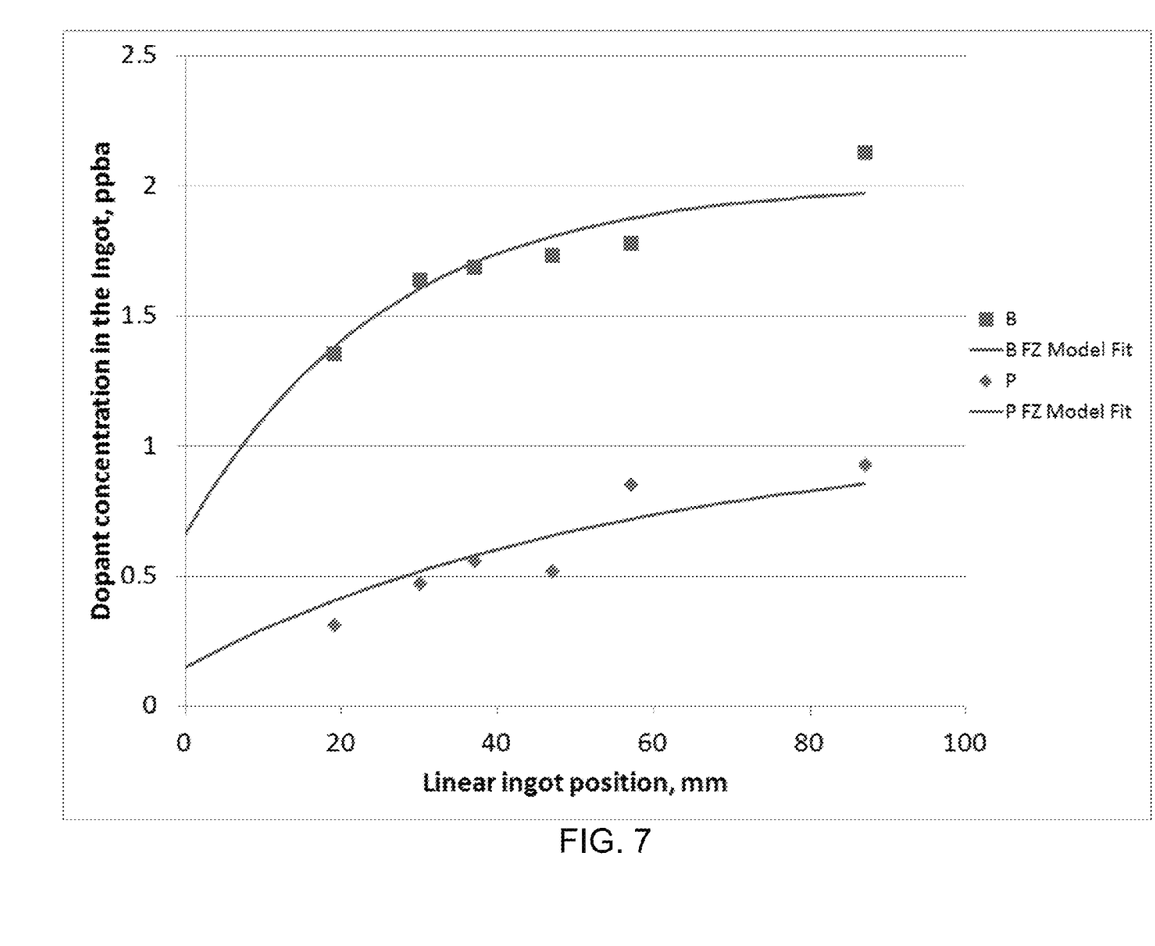
FIG. 7 is a graph of dopant concentration versus linear ingot position for the ingot of FIG. 5, which shows the concentrations of boron and phosphorus in the ingot as a function of the distance along the ingot; the concentrations were measured by low-temperature Fourier transform infrared spectroscopy.
Figure 8:
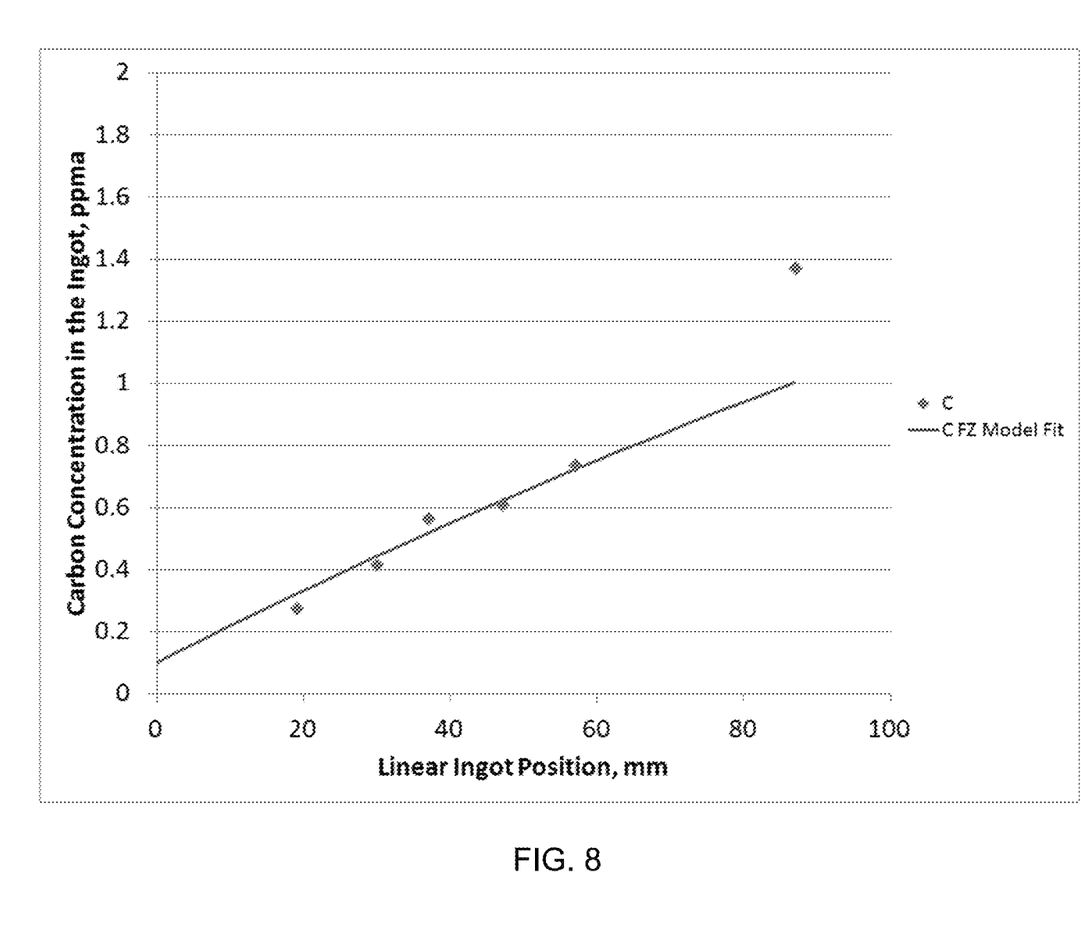
FIG. 8 is a graph of dopant concentration versus linear ingot position for the ingot of FIG. 5, which shows the concentration of carbon in the ingot as a function of the distance along the ingot; the concentration was measured by low-temperature Fourier transform infrared spectroscopy.

The ingot shown in FIG. 5 was sliced and polished into 2.5-mm thick discs for LTFTIR analysis. The ingot had a mass of 17.84 g and a length of 105 mm. The slug used had a mass of 2.00 grams and contained 1 ppta P, 3 ppta B, and 1 ppba C. Discs obtained at distances of 19, 30, 37, 47, 57, and 87 mm from the starting end of the ingot were analyzed. FIG. 7 is a graph of dopant concentration versus linear ingot position, which shows the concentrations of boron and phosphorus in the ingot ($C^l_s(x)$) as a function of the distance along the ingot. FIG. 8 is a graph of dopant concentration versus linear ingot position, which shows the concentration of carbon in the ingot as a function of the distance along the ingot. The concentration of each element in the silicon granules ($C_o$) was determined using the boat zoning mass balance equation:

$$C^l_S(x) = C_O\left(1 - \left(1 - k\left(\frac{(V_{ZONE} - V_{SLUG}) + \left(C^l_{SLUG} * \frac{V_{SLUG}}{C_O}\right)}{V_{ZONE}}\right)\right)e^{\frac{kx}{l}}\right)$$

where l is 20 mm (the length of the melt zone as determined by the induction coil size), and x is the position of each disc along the length. The equilibrium segregation coefficient k is 0.8 for boron, 0.35 for phosphorus, and 0.07 for carbon.

Example 3

Trace Elements Analysis—II

Three ingots produced from the same source of granular silicon by using the boat zoner method were analyzed by the same LTFTIR method to verify reproducibility. The initial concentrations of B, P, and C in the silicon granules as determined from the measurements in three ingots are shown in Table 2. For comparison, four single crystal ingots pulled from the same source of granular silicon material at the Institute of Crystallization in Germany (IKZ) were analyzed using the same LTFTIR method, and the initial concentrations, $C_o$, based on the measured concentrations were calculated. The initial concentration results in the granules are compared in Table 2. Results show that B, P, and C concentrations from the three boat zoner multicrystalline samples and the four IKZ single crystal samples were similar based on a t-test performed with 95% statistical confidence.

TABLE 2

Initial concentrations of B, P, and C in granules

| Ingot # | Method | Crystal structure | P ppba | B ppba | C ppma |
|---|---|---|---|---|---|
| 1 | Boat Zoner | multi | 0.9 | 3.1 | 4.7 |
| 2 | Boat Zoner | multi | 1.1 | 2.2 | 3.3 |
| 3 | Boat Zoner | multi | 1.0 | 2.0 | 3.2 |
| | Boat Zoner Average | | 1.0 | 2.4 | 3.8 |
| | Boat Zoner Standard Deviation | | 0.11 | 0.58 | 0.85 |
| 4 | IKZ | single | 1.2 | 3.5 | 7.5 |
| 5 | IKZ | single | 1.8 | 2.1 | 18 |
| 6 | IKZ | single | 0.7 | 2.1 | 6.8 |
| 7 | IKZ | single | 0.5 | 2.0 | 5.7 |
| | IKZ Average | | 1.0 | 2.4 | 9.5 |
| | IKZ Standard Deviation | | 0.56 | 0.74 | 5.8 |

Example 4

Trace Elements Analysis—III

Figure 9:
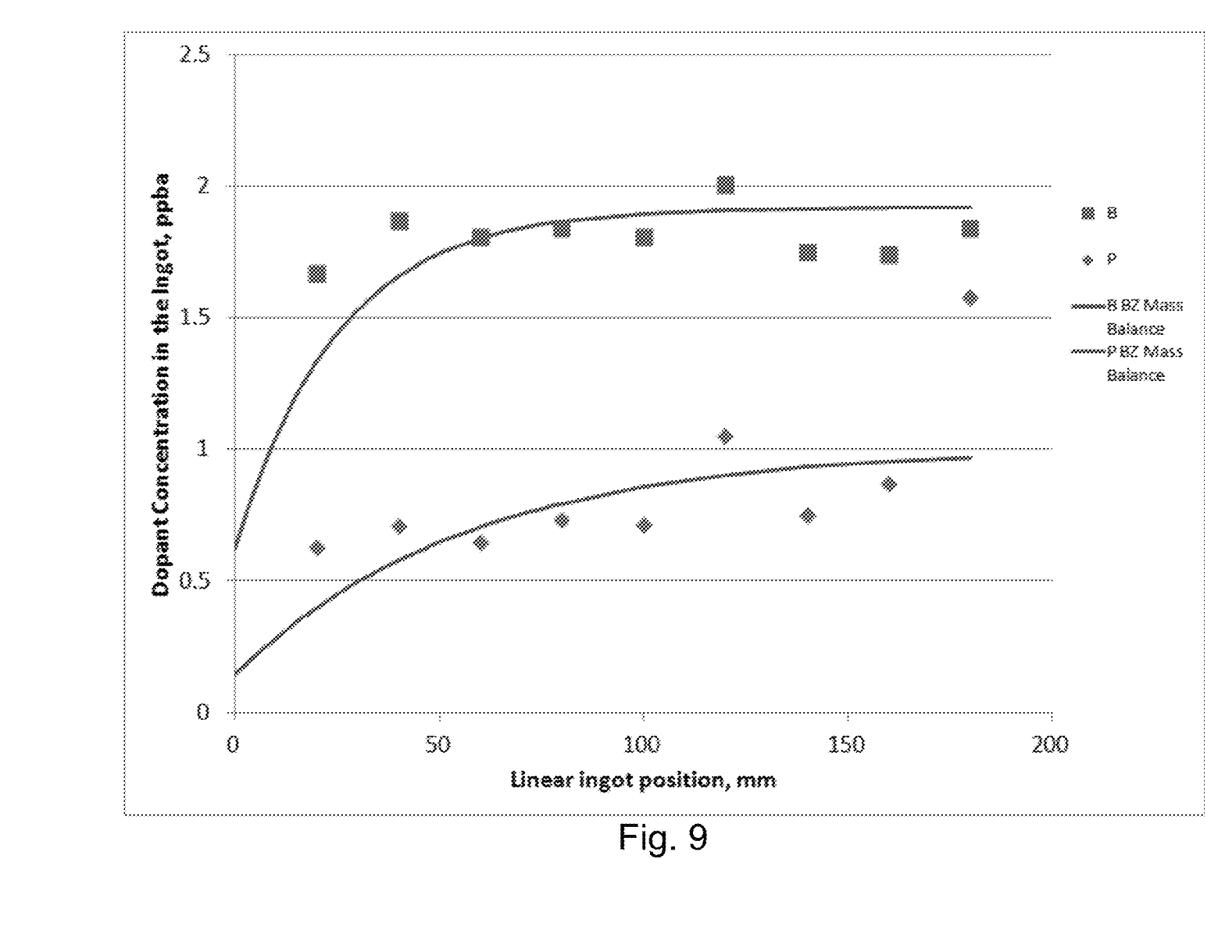
FIG. 9 is a graph of dopant concentration versus linear ingot position for the ingot of FIG. 6, which shows the measured and predicted concentrations of boron and phosphorus in the ingot as a function of the distance along the ingot.
Figure 10:
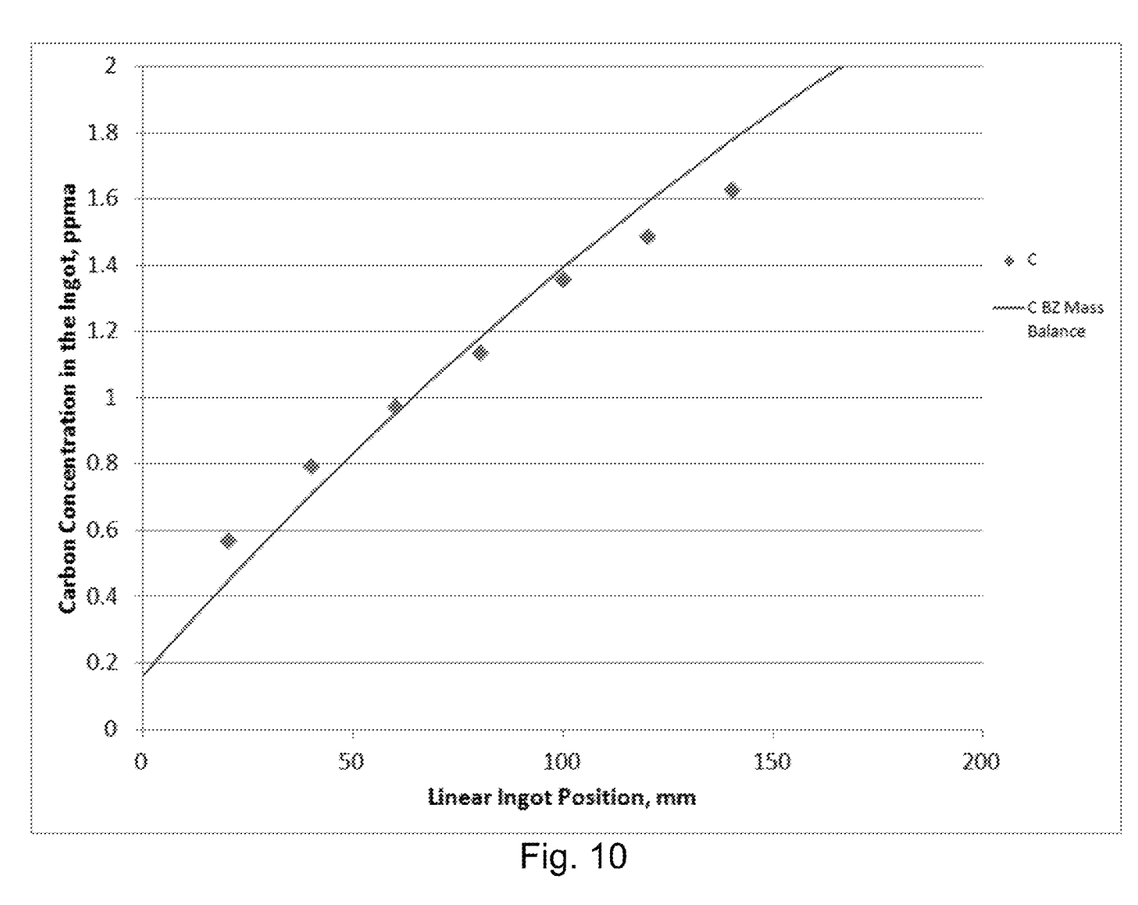
FIG. 10 is a graph of dopant concentration versus linear ingot position for the ingot of FIG. 6, which shows the measured and predicted concentration of carbon in the ingot as a function of the distance along the ingot.

In another example, a longer multicrystalline silicon ingot, e.g., 200 mm, (FIG. 6) was produced using a longer vessel. The ingot had a mass of 33.63 g and a length of 190 mm. The slug used had a mass of 2.11 grams and contained 3.8 ppta P, 0 ppta B, and 1 ppba C. FIG. 9 is a graph of dopant concentration versus linear ingot position for the 190 mm long ingot, which shows the measured and predicted concentrations of boron and phosphorus in the ingot as a function of the distance along the ingot. FIG. 10 is a graph of dopant concentration versus linear ingot position for the 190 mm long ingot, which shows the measured and predicted concentration of carbon in the ingot as a function of the distance along the ingot. Initial concentrations in the granular silicon are predicted as 1.01 ppba P, 1.92 ppba B, and 4.33 ppma C.

To assess any contamination introduced by the boat zoner consolidation method, a very high purity silicon rod with known B, P, and C, concentrations, produced by the Siemens method, was processed using the boat zoner method and converted into a multicrystalline silicon ingot. Phosphorus, boron, and carbon in each sample were determined by LTFTIR. The Siemens rod included 0.003 ppba phosphorus, 0 ppba boron, and 0.001 ppma carbon. The multicrystalline silicon ingot included 0.055 ppba phosphorus, 0 ppba boron, and 0.050 ppma carbon, which were well within the target levels of 0.5 ppba for phosphorus and boron, and 0.25 ppma for carbon. Given the fact that the multicrystalline silicon ingot was not produced in a clean room environment, the disclosed consolidation method did not significantly increase trace element levels within the multicrystalline silicon ingot compared to the Siemens rod.

In view of the many possible embodiments to which the principles of the disclosed invention may be applied, it should be recognized that illustrated embodiments are only preferred examples of the invention and should not be taken as limiting the scope of the invention. Rather, the scope of the invention is defined by the following claims.

We claim:

1. A method of converting a sample of silicon granules into a form suitable for measurement of the purity of the silicon, the method comprising:
    placing a volume of silicon granules into a vessel having a surface that defines an upwardly opening cavity having a capacity of ≤500 cm³ and in which the volume of silicon granules is received, the cavity having a leading end and a trailing end;

embedding a silicon slug of known purity at least partially in the volume of silicon granules near the leading end;

positioning the vessel to pass through an induction coil of an induction heater, the induction coil defining an axially extending passageway sized such that the vessel can pass through the passageway, wherein at least one of the vessel and the induction coil is configured to move axially relative to the other of the vessel and the induction coil;

heating the silicon slug with a preheater comprising conductive silicon carbide to a temperature sufficient to couple the silicon slug with the induction heater, wherein the preheater is configured to heat contents of the cavity;

inductively heating the preheated silicon slug to a temperature sufficient to melt at least a portion of the preheated silicon slug to form a silicon melt; and moving the vessel or the induction coil generally horizontally such that the vessel passes through the induction coil at a rate to successively inductively heat and melt regions of the volume of silicon granules from the leading end to the trailing end with each region solidifying as the molten silicon exits the induction coil to provide a multicrystalline silicon ingot in the cavity.

2. The method of claim 1, wherein the silicon granules have an average diameter of less than 10 mm.

3. The method of claim 1, wherein the silicon slug is preheated to a temperature of at least 1000° C.

4. The method of claim 1, wherein the silicon slug has known concentrations of boron, phosphorus, and carbon.

5. The method of claim 1, wherein the silicon slug comprises less than 10 ppta (parts per trillion atoms) boron and phosphorus.

6. The method of claim 1, wherein the induction heater is operated at 300-3000 kHz.

7. The method of claim 1, wherein the preheater is inductively coupled to the induction coil during the heating of the silicon slug with the preheater.

8. The method of claim 1, further comprising placing the vessel within a shield device such that the shield device covers the upwardly opening cavity.

9. The method of claim 8, further comprising:
purging an interior space defined by the shield device with an inert gas; and
sealing the shield device, thereby excluding air from the interior space.

10. The method of claim 1, wherein the induction coil is configured to provide a melting zone having a length of 20-30 mm.

11. The method of claim 1, wherein the vessel is passed through the induction coil at a rate of up to 5 mm/minute.

12. The method of claim 1, further comprising:
removing the multicrystalline silicon ingot from the vessel;
slicing a wafer from the multicrystalline silicon ingot; and
determining levels of trace elements in the wafer.

13. The method of claim 12, wherein the determining comprises:
(i) measuring the content of one or more of boron, phosphorus, carbon, aluminum, and oxygen;
(ii) performing low-temperature Fourier transform infrared spectroscopy (LTFTIR) analysis; or
(iii) both (i) and (ii).

14. A granule consolidation apparatus, comprising:
a vessel having a surface that defines an upwardly opening cavity having a capacity of ≤500 cm$^3$;
an induction heater comprising an induction coil defining an axially extending passageway sized such that the vessel can pass through the passageway, wherein at least one of the vessel and the induction coil is configured to move axially relative to the other of the vessel and the induction coil; and
a preheater comprising conductive silicon carbide, wherein the preheater is configured to heat contents of the cavity.

15. The granule consolidation apparatus of claim 14, wherein the preheater has a ring configuration defining an axially extending passageway sized such that the vessel can pass through the passageway.

16. The granule consolidation apparatus of claim 14, wherein the preheater is configured to move relative to the induction coil.

17. The granule consolidation apparatus of claim 14, further comprising a shield device configured to surround the vessel.

18. The granule consolidation apparatus of claim 14, wherein the vessel further defines an internal chamber having an inlet and an outlet.

19. The granule consolidation apparatus of claim 14, wherein the upwardly opening cavity has a length of at least 10 cm and a greatest width from 5 mm to 15 mm.

20. The granule consolidation apparatus of claim 14, wherein the vessel is constructed of a metal.

* * * * *